United States Patent
Armstrong et al.

(10) Patent No.: US 7,918,826 B2
(45) Date of Patent: Apr. 5, 2011

(54) TROCAR ASSEMBLY

(75) Inventors: Glen A. Armstrong, Liberty Township, OH (US); Thomas A. Gilker, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 149 days.

(21) Appl. No.: 11/855,777

(22) Filed: Sep. 14, 2007

(65) Prior Publication Data

US 2009/0076456 A1 Mar. 19, 2009

(51) Int. Cl.
*A61M 5/178* (2006.01)

(52) U.S. Cl. ............... 604/167.03; 604/167.05

(58) Field of Classification Search ......... 604/164.01–164.13, 165.01–165.04, 604/167.01–167.06

See application file for complete search history.

(56) References Cited

U.S. PATENT DOCUMENTS

| | | | |
|---|---|---|---|
| 4,809,694 A * | 3/1989 | Ferrara | 606/130 |
| 5,104,383 A | 4/1992 | Shichman | |
| 5,180,373 A | 1/1993 | Green et al. | |
| 5,197,955 A | 3/1993 | Stephens et al. | |
| 5,209,737 A | 5/1993 | Ritchart et al. | |
| 5,226,891 A | 7/1993 | Bushatz et al. | |
| 5,391,154 A | 2/1995 | Young | |
| 5,395,342 A | 3/1995 | Yoon | |
| 5,443,452 A | 8/1995 | Hart et al. | |
| 5,476,475 A | 12/1995 | Gadberry | |
| 5,492,304 A | 2/1996 | Smith et al. | |
| 5,542,931 A | 8/1996 | Gravener et al. | |
| 5,545,142 A | 8/1996 | Stephens et al. | |
| 5,545,179 A | 8/1996 | Williamson, IV | |
| 5,584,850 A | 12/1996 | Hart et al. | |
| 5,603,702 A | 2/1997 | Smith et al. | |
| 5,628,732 A | 5/1997 | Antoon, Jr. et al. | |
| 5,720,759 A | 2/1998 | Green et al. | |
| 5,788,676 A | 8/1998 | Yoon | |
| 5,792,113 A | 8/1998 | Kramer et al. | |
| 5,814,026 A | 9/1998 | Yoon | |
| 5,906,595 A | 5/1999 | Powell et al. | |
| 6,482,181 B1 | 11/2002 | Racenet et al. | |
| 6,551,282 B1 * | 4/2003 | Exline et al. | 604/167.01 |
| 6,595,946 B1 | 7/2003 | Pasqualucci | |
| 6,702,787 B2 | 3/2004 | Racenet et al. | |
| 6,942,671 B1 * | 9/2005 | Smith | 606/108 |
| 6,981,966 B2 | 1/2006 | Green et al. | |
| 7,025,747 B2 | 4/2006 | Smith | |
| 7,052,454 B2 | 5/2006 | Taylor | |
| 7,112,185 B2 | 9/2006 | Hart et al. | |
| 7,165,568 B2 | 1/2007 | Kessell et al. | |

(Continued)

FOREIGN PATENT DOCUMENTS

EP 0568383 11/1993

(Continued)

*Primary Examiner* — Theodore J Stigell (57) ABSTRACT

Methods and devices for accessing a body cavity are disclosed. In general, a trocar assembly is provided that can include a housing having a cannula that extends therefrom to define a working channel that is sized and configured to receive a surgical instrument. The trocar assembly can also include a seal unit that is disposed in the housing. The seal unit can be generally configured to allow off-axis insertion of an instrument through the working channel without lateral movement of the seal unit. For example, in one exemplary embodiment, the seal unit can be rotatably disposed in the housing and have at least one seal element that is adapted to selectively seal the working channel. The seal unit can also be adapted to rotate about a longitudinal axis of the assembly and an axis perpendicular thereto.

27 Claims, 7 Drawing Sheets

U.S. PATENT DOCUMENTS

| | | |
|---|---|---|
| 2003/0004529 A1 | 1/2003 | Tsonton et al. |
| 2004/0106942 A1 | 6/2004 | Taylor et al. |
| 2004/0230161 A1 | 11/2004 | Zeiner |
| 2004/0256004 A1 | 12/2004 | Kessell et al. |
| 2005/0033342 A1 | 2/2005 | Hart et al. |
| 2005/0059865 A1 | 3/2005 | Kahle et al. |
| 2005/0059934 A1 | 3/2005 | Wenchell et al. |
| 2005/0070946 A1 | 3/2005 | Franer et al. |
| 2005/0077689 A1 | 4/2005 | Hueil |
| 2005/0131349 A1 | 6/2005 | Albrecht et al. |
| 2005/0203543 A1 | 9/2005 | Hilal et al. |
| 2005/0212221 A1 * | 9/2005 | Smith et al. .................. 277/628 |
| 2005/0216028 A1 | 9/2005 | Hart et al. |
| 2006/0211992 A1 * | 9/2006 | Prosek .................. 604/167.06 |
| 2006/0217666 A1 * | 9/2006 | Wenchell ................ 604/167.03 |
| 2007/0185453 A1 | 8/2007 | Michael et al. |
| 2008/0046000 A1 | 2/2008 | Lee et al. |

FOREIGN PATENT DOCUMENTS

| | | |
|---|---|---|
| EP | 0731718 | 9/1996 |
| EP | 1284664 | 2/2003 |
| EP | 1679043 | 7/2006 |
| EP | 1698291 | 9/2006 |
| EP | 1707133 | 10/2006 |
| EP | 1709918 | 10/2006 |
| WO | WO-9604946 | 2/1996 |

* cited by examiner

TROCAR ASSEMBLY

FIELD OF THE INVENTION

The present invention relates to methods and devices for accessing a body cavity.

BACKGROUND OF THE INVENTION

Minimally invasive surgical procedures including, for example, endoscopic, laparoscopic, and arthoscopic procedures, allow a surgeon to perform a complex surgical procedure with minimal incisions into the skin and tissue surrounding a particular body cavity or anatomical region. In order to gain access to a body cavity, it is often necessary to puncture and cannulate the body cavity using a surgical access device such as a trocar. A trocar assembly generally includes a trocar housing with a cannula extending therefrom and a trocar obturator that is inserted through the cannula. In use, the trocar cannula, with the obturator extending therethrough, is pierced through the skin to access a body cavity. To penetrate the skin, the distal end of the trocar cannula is placed against an incision in the skin and pressure is applied to the proximal end of the trocar to force the sharp point of the obturator through the skin until it enters the targeted body cavity. The obturator can then be withdrawn, leaving the cannula as an access way to the targeted body cavity.

Generally, the proximal end of the trocar cannula is joined to a trocar housing that defines a chamber having an open distal end portion in communication with the interior lumen defined by the trocar cannula. The trocar obturator, as well as other elongated surgical instruments or tools, axially extend into and are withdrawn from the trocar cannula through the proximal end portion of the chamber defined by the trocar housing.

In use, it is important to maintain a substantially closed environment during insertion or withdrawal of instruments through the trocar assembly so as to preserve sterility of the treatment site in addition to preventing the escape of liquids and/or insufflation gas. Typically, a seal element is disposed within the housing in an attempt to provide such an environment. However, if an instrument is delivered off-axis relative to the cannula, the effectiveness of the seal may diminish, as off-axis delivery results in a disproportionate force being applied to one portion of the seal. This can result in non-uniform deformation of the seal which can reduce the seal's ability to effectively engage an outer surface of an instrument thereby resulting in contamination of the site and/or escape of liquids and/or insufflation gas from the cannula.

Accordingly, there remains a need for devices and methods configured to allow for the efficient and reliable delivery of a surgical instrument to a treatment site.

SUMMARY OF THE INVENTION

The present invention provides methods and devices for accessing a body cavity. In general, a trocar assembly is provided that can include a housing having a cannula that extends therefrom to define a working channel that is sized and configured to receive a surgical instrument. The trocar assembly can also include a seal unit that is disposed in the housing. While a variety of configurations are available for the seal unit, the seal unit can be generally configured to allow off-axis insertion of an instrument through the working channel without lateral movement of the seal unit. For example, in one exemplary embodiment, the seal unit can be rotatably disposed in the housing and have at least one seal element that is adapted to selectively seal the working channel. The seal unit can be adapted to rotate about a longitudinal axis of the assembly and an axis perpendicular thereto. The seal unit can also be adapted to rotate about its center.

In one exemplary embodiment, the at least one seal element can be disposed in an approximately spherically shaped member at a position that is between opposed poles of the spherically shaped member. The seal element can be formed from virtually any type of seal including, but not limited to, a zero-closure seal. The spherically shaped member can be formed from a rigid material and can include a bore that extends therethrough. In one embodiment, the bore can include angular lead-ins that are formed at the proximal and distal ends thereof. The spherically shaped member can be disposed in the housing such that a longitudinal axis of the bore aligns with the longitudinal axis of the working channel when the assembly is in a natural condition. In one embodiment, the spherically shaped member can be secured in the housing by an O-ring that is disposed proximal to the at least one seal element and a U-ring that is disposed distal to the at least one seal element. The U-ring can be positioned at a point that is distal to a center line of the spherically shaped member.

In another exemplary embodiment, the trocar assembly can further include a second seal element. In general, the second seal element can be disposed distal to the seal unit. Virtually any type of seal can form the second seal element including, for example, a zero-closure seal such as a duckbill seal.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides methods and devices for accessing a body cavity. In general, a trocar assembly is provided that can include a housing having a cannula that extends therefrom to define a working channel that is sized and configured to receive a surgical instrument. The trocar assembly can also include a seal unit that is disposed in the housing. While a variety of configurations are available for the seal unit, the seal unit can be generally configured to allow off-axis insertion of an instrument through the working channel substantially without lateral movement of the seal unit. For example, in one exemplary embodiment, the seal unit can be rotatably disposed in the housing and have at least one seal element that is adapted to selectively seal the working channel. The seal unit can also be adapted to rotate about a longitudinal axis of the assembly and an axis perpendicular thereto.

Figure 1:
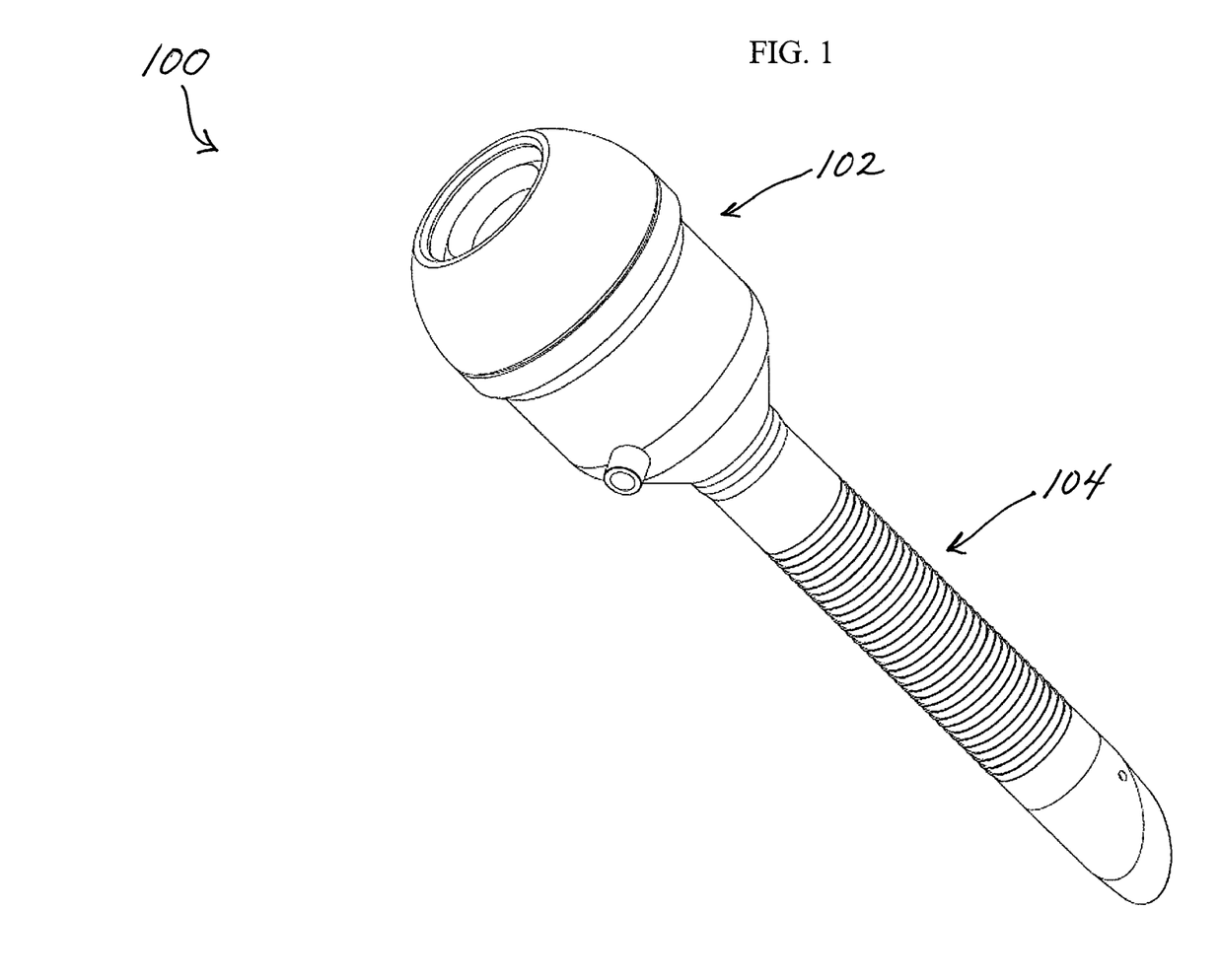
FIG. 1 is a perspective view of one embodiment of a device for accessing a body cavity.
Figure 2:
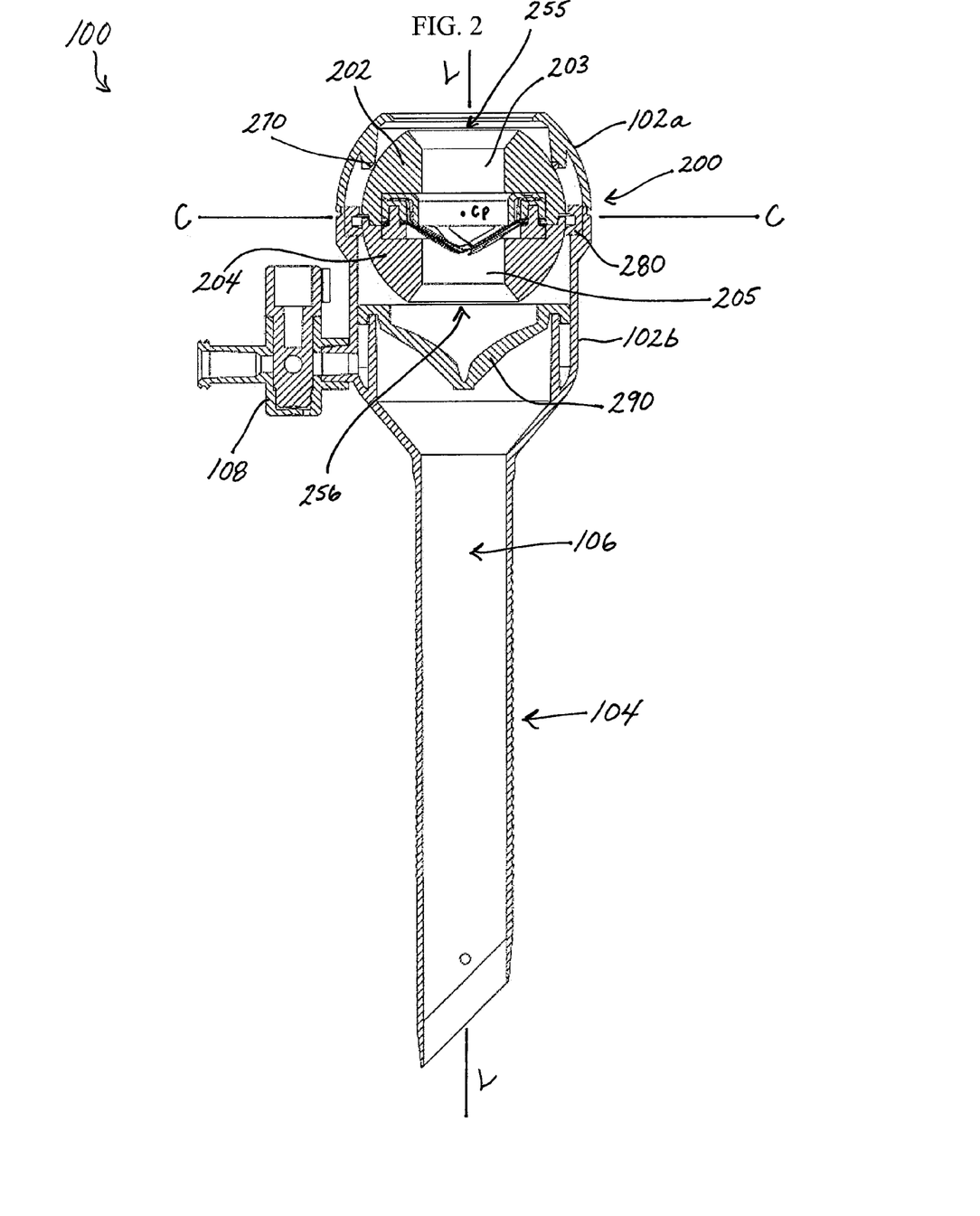
FIG. 2 is a cross-sectional view of the device shown in FIG. 1.
Figure 2A:
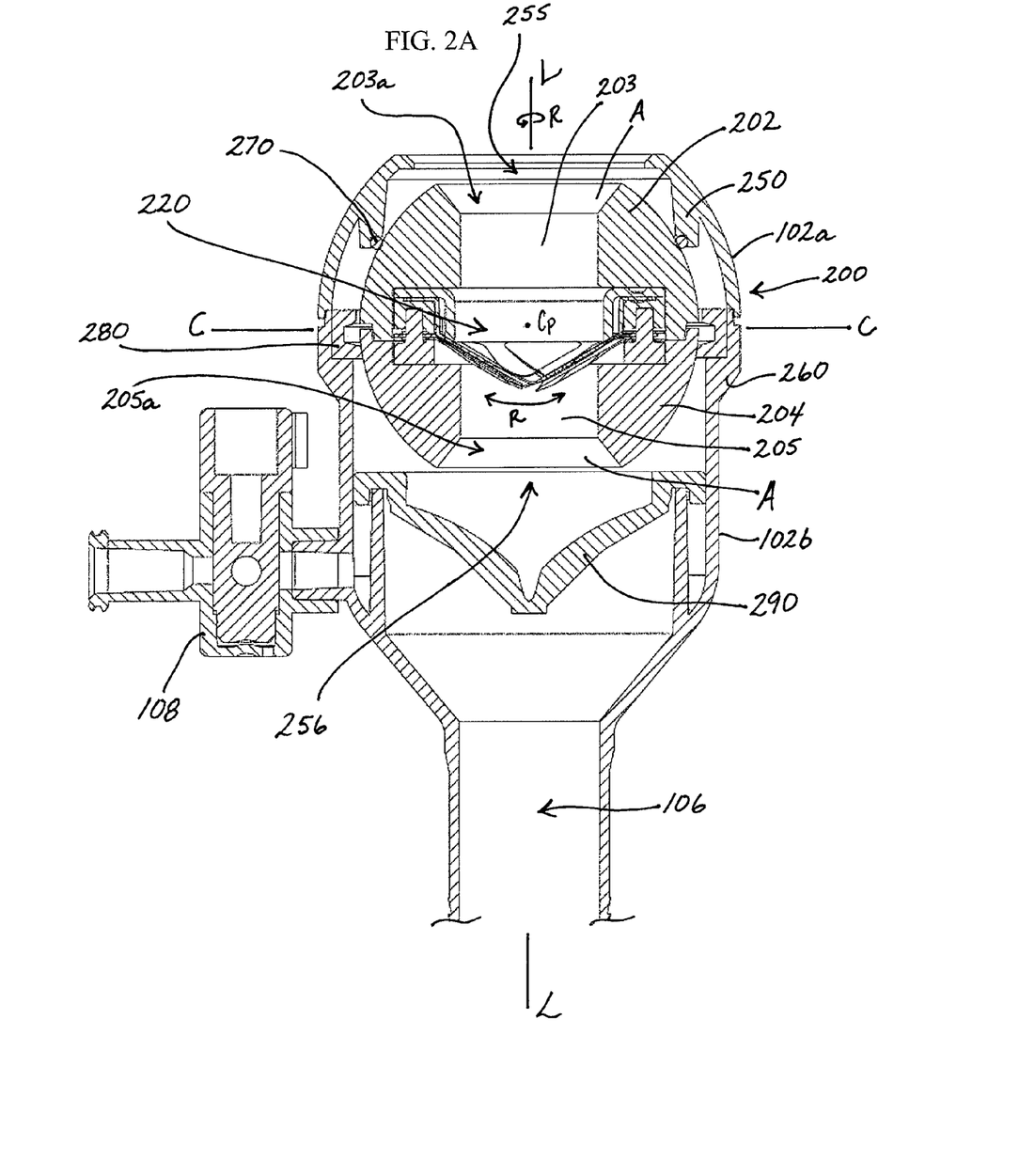
FIG. 2A is a cross-sectional view of the proximal portion of the device shown in FIG. 1.
Figure 3:
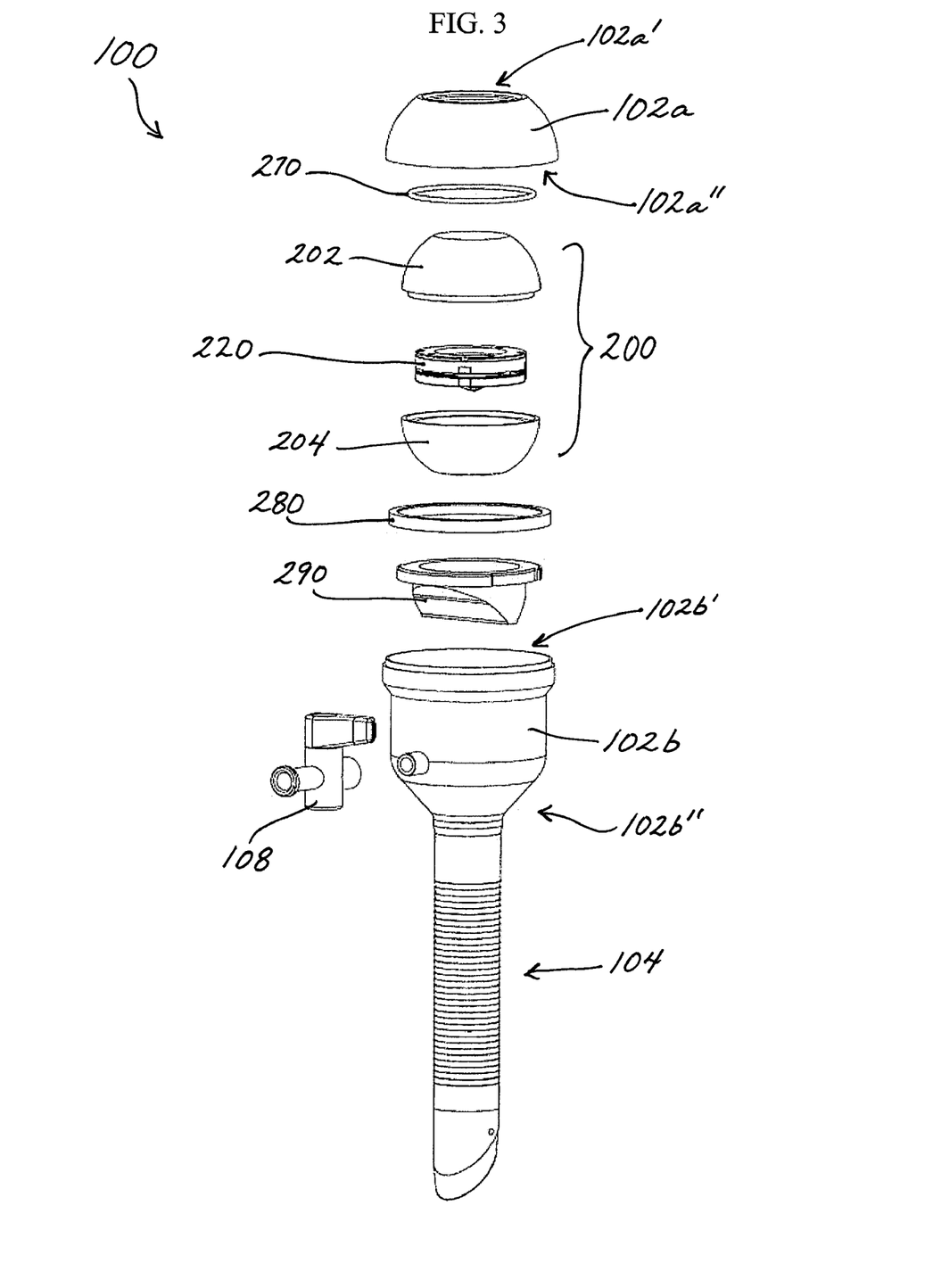
FIG. 3 is an exploded view of the device shown in FIG. 1.

FIG. 1 illustrates one exemplary embodiment of a trocar assembly 100. As shown, the trocar assembly 100 generally includes a housing 102 with a cannula 104 that extends distally therefrom. A number of configurations are available for the housing 102. For example, as shown in FIGS. 2-5, the housing 102 includes a top portion 102a and a bottom portion 102b. The top portion 102a of the housing 102 can have a variety of shapes including the generally semi-spherical shape shown in FIG. 1. Further, the top portion 102a of the housing 102 can have an open proximal end portion 102a' and an open distal end portion 102a" (FIG. 3). The proximal end portion 102a' can define an opening that is adapted to receive an instrument, and the distal end portion 102a" can be configured to mate to or be coupled to a proximal end 102b' of the bottom portion 102b of the housing 102. The bottom portion 102b of the housing 102 can include a proximal end 102b' that is adapted to mate to the top portion 102a of the housing 102 and a distal end 102b" that can be configured to mate to or be coupled to a proximal end 104a of the cannula 104. A variety of techniques can be used to mate the top portion 102a of the housing 102 to the bottom portion 102b of the housing 102 including, but not limited to, snap-fits, interference fits, threaded engagements, and other bonding techniques including ultrasonic welding.

Similar to the housing 102, the cannula 104 can also have an open distal end portion and an open proximal end portion (not shown). The proximal end portion can extend into and be mounted or otherwise coupled to the open distal end 102b" of the housing 102. The cannula 104 can extend distally from the housing 102 to define an inner lumen or working channel 106 (FIG. 2) that is sized and configured to receive a surgical instrument. One skilled in the art will appreciate that the bottom portion 102b of the housing 102 and the cannula 104 can be formed as a unitary structure or as two separate components that are mated to one another. The housing 102 can also include a stop-cock valve 108 for allowing and preventing the passage of an insufflation fluid, e.g. carbon dioxide, through flexible tubing (not shown) and into a portion of the housing 102 and cannula 104.

As indicated above, the trocar assembly 100 can also include a seal unit 200. In one exemplary embodiment, shown in FIGS. 2-5, the trocar assembly 100 includes a seal unit 200 that is disposed in the housing 102. In general, the seal unit 200 can be configured to allow off-axis insertion of an instrument through the working channel 106 of the assembly 100 substantially without lateral movement of the seal unit 200. A variety of configurations are available including, for example, a seal unit 200 that is rotatably disposed in the housing 102 and having at least one seal element 220 that is adapted to selectively seal the working channel 106 of the assembly 100. The rotatably disposed seal unit 200 can be adapted to rotate about at least one of a longitudinal axis L of the assembly 100 and an axis that is perpendicular thereto.

Figure 4:
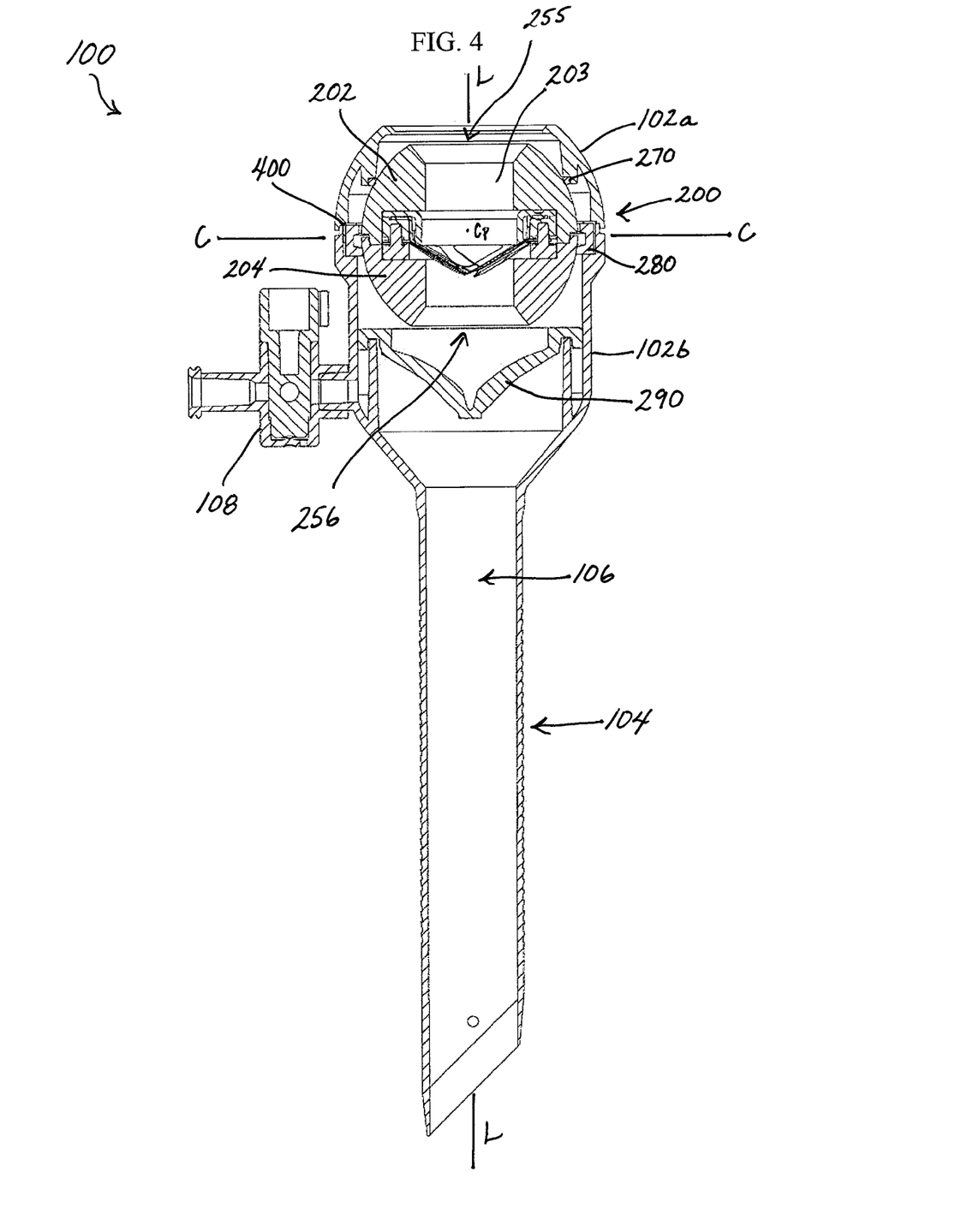
FIG. 4 is a cross-sectional view of another embodiment of a device for accessing a body cavity.
Figure 4A:
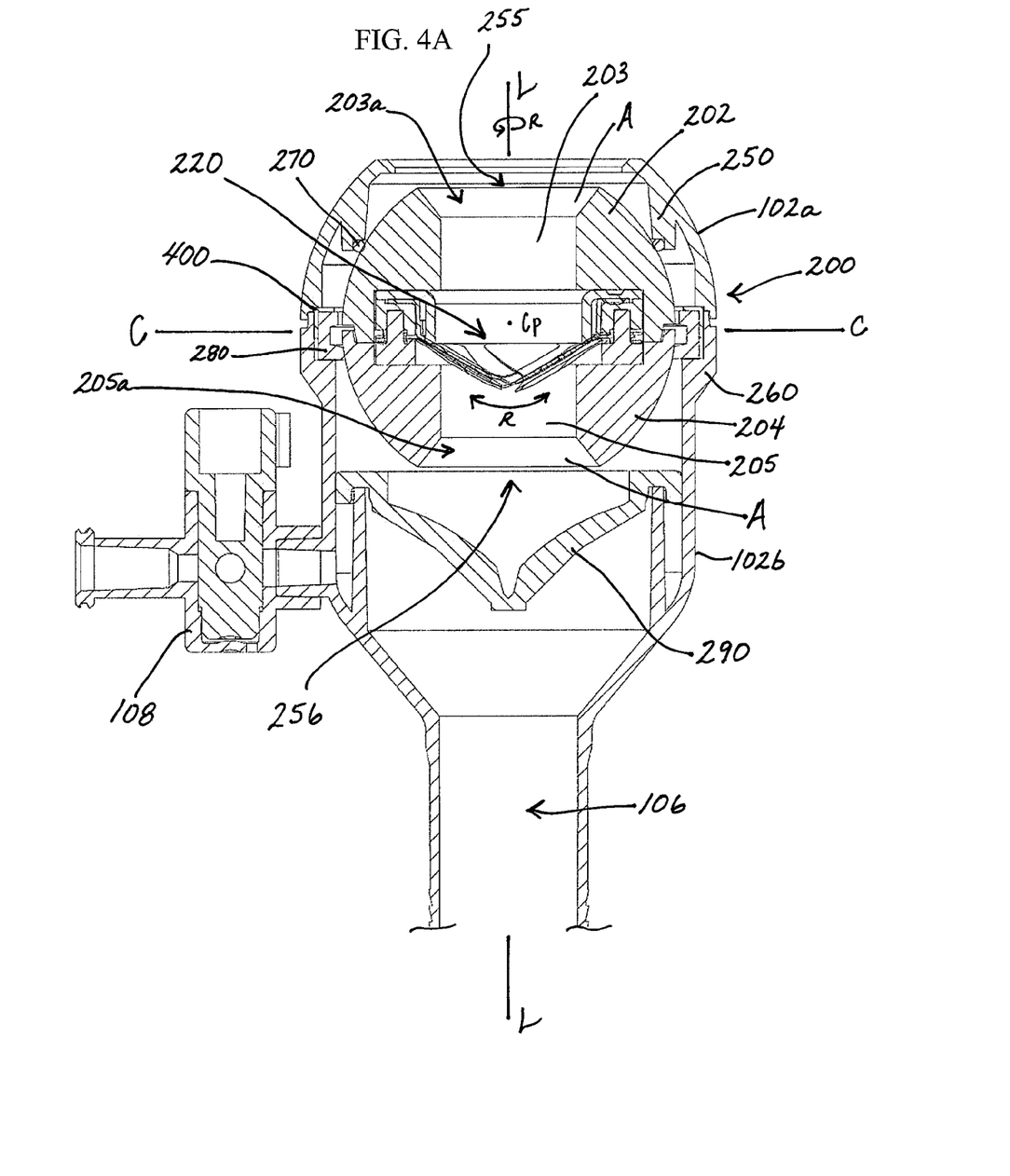
FIG. 4A is a cross-sectional view of the proximal portion of the device shown in FIG. 4.
Figure 5:
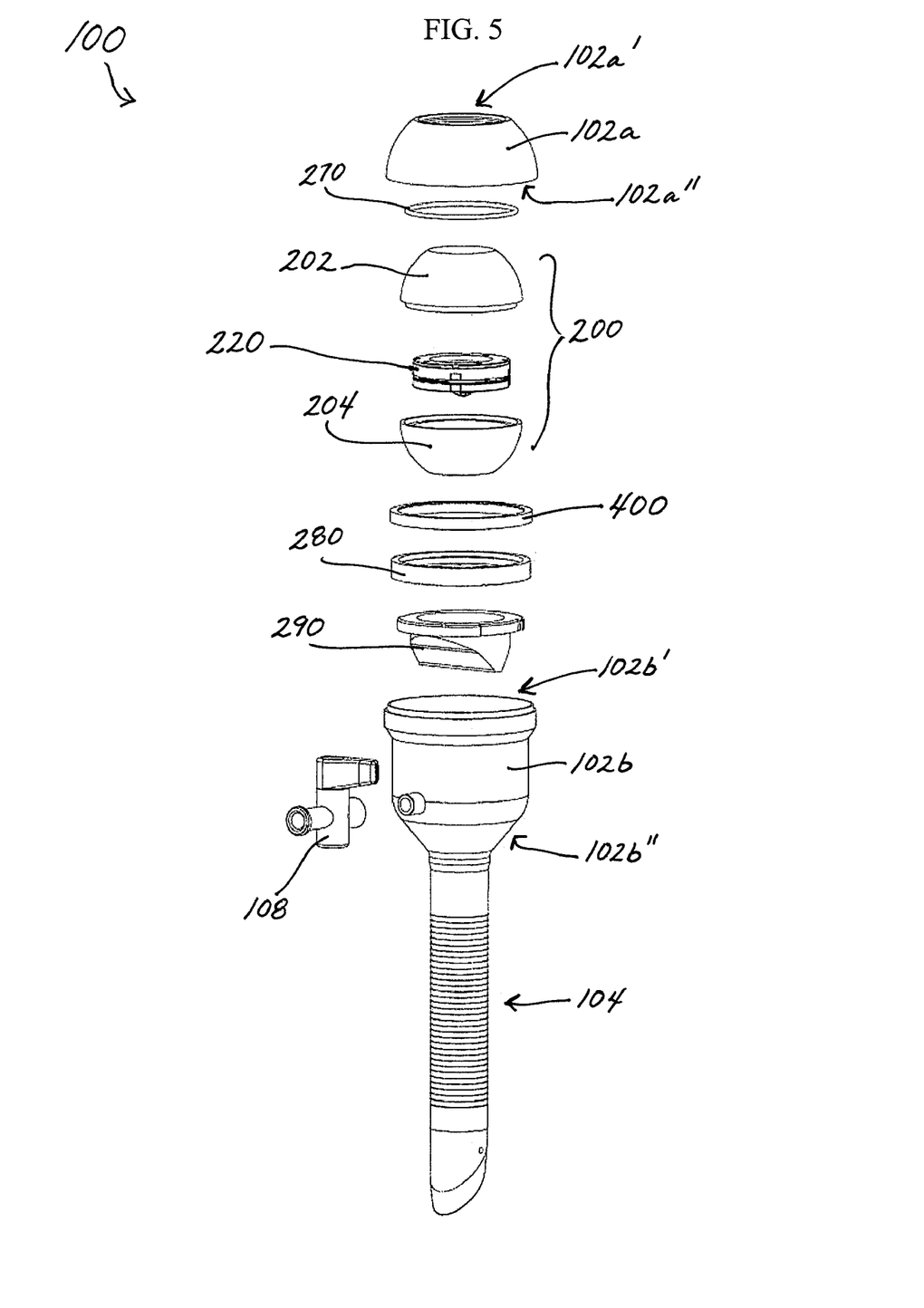
FIG. 5 is an exploded view of the device shown in FIG. 4.

FIGS. 2-5 illustrate an exemplary embodiment of a seal unit 200 that takes the form of a substantially spherically shaped member. The seal unit 200 can include at least one seal element disposed therein. In general, the at least one seal element can be positioned between opposed poles of the substantially spherically shaped seal unit 200. For example, as shown in FIGS. 2-5, the at least one seal element 220 is positioned distal to the north or proximal pole 255 of the seal unit 200 and proximal to the distal or south pole 256 of the seal unit 200. As illustrated in FIGS. 2-5, the seal element 220 is positioned approximately at the equator or center line C of the seal unit 200. In one exemplary embodiment, the at least one seal element 220 can be sandwiched between upper and lower portions 202, 204 of the spherically shaped seal unit 200. The upper and lower portions 202, 204 can each have a bore 203, 205 extending therethrough. Each bore can include an angular lead-in A. As shown in FIGS. 2A and 4A, the upper portion 202 includes an angular lead-in A formed at the proximal end 203a of the bore 203 and the lower portion 204 includes an angular lead-in A formed at the distal end 205a of the bore 205. The angular lead-ins A can be adapted to facilitate the insertion of an instrument into the housing 102 and guide the instrument through the working channel 106 of the assembly 100. The bores 203, 205 can be formed in the upper and lower portions 202, 204 such that the bores 203, 205 align to form one continuous bore when the upper and lower portions 202, 204 are coupled to each other. As shown in FIGS. 2A and 4A, the longitudinal axis of the bore aligns with the longitudinal axis L of the working channel when the assembly 100 is in a natural condition (i.e., when no instrument is inserted therethrough).

Several techniques can be used to couple the upper and lower portions 202, 204 of seal unit 200. In one embodiment, shown in FIGS. 2-3, the upper and lower portions 202, 204 are held together by support shoulders 250 and lap joints 260 formed on an inner surface of the housing 102. In another embodiment, shown in FIGS. 4-5, a compression ring 400 is disposed around the spherically shaped member to secure together the upper and lower portions 202, 204. The upper and lower portions 202, 204 of the spherically shaped member can be formed from a variety of materials. In general, the spherically shaped member can be formed from a rigid material such as, for example, molded polycarbonate. One skilled in the art will appreciate that a number of alternative rigid materials can be used to form the spherically shaped member.

A variety of techniques can be used to rotatably dispose the spherically shaped seal unit 200 in the housing 102 of the trocar assembly 100. In one exemplary embodiment, shown in FIGS. 2-5, the seal unit 200 can be captured in the housing 102 by two separate ring-type silicon seals. For example, the spherically shaped member can be secured in the housing 102 by an O-ring 270 that is disposed proximal to the at least one seal element 220 and a U-ring 280 that is disposed distal to the at least one seal element 220. The U-ring 280 can provide the primary point of capture. As shown in FIGS. 2A and 4A, the U-ring 280 is generally disposed around the lower portion 204 of the spherically shaped member at a point that is just distal to the center line C of the member and in a horizontal plane that is perpendicular to the longitudinal axis L of the trocar assembly 100. Positioning the U-ring 280 slightly below the center line C can be effective to inhibit the spherically shaped member from being driven distally through the housing 102. Referring back to FIG. 2A, the U-ring 280 is skewed at a slight angle about the longitudinal axis L of the assembly 100 to form a U-shaped seat to support and seal the spherically shaped member in the housing 102. The U-ring 280 can be held in this configuration by the support shoulders 250 and lap joints 260 formed on the inner surface of the housing 102. The second point of capture can be accomplished by an O-ring 270 that is held in a plane parallel to the U-ring 280 but around the upper portion 202 of the spherically shaped member and at a point that is distal to the proximal end 203a of the bore 203 of the upper portion 202 and proximal to the seal element 220. The dual O- and U-ring configuration can create a slightly compressed state that can be effective to capture and seal around the perimeter of the spherically shaped member. Such a configuration can also inhibit any lateral movement of the spherically shaped member while allowing the member to rotate about the longitudinal axis L of the assembly 100 and an axis perpendicular thereto.

As shown in FIGS. 2A and 4A, arrows R indicate that the seal unit 200 is adapted to rotate about both the longitudinal axis L of the assembly 100 and an axis perpendicular thereto. Although the seal unit 200 is shown and described as being adapted to rotate about both the longitudinal axis L and an axis perpendicular thereto, one skilled in the art will appreciate that rotation of the seal unit 200 can be limited and the seal unit 200 need not be adapted to rotate about both axes. In one exemplary embodiment, shown in FIGS. 2-5, the substantially spherically shaped seal unit 200 is adapted to rotate about its center Cp. As illustrated in FIGS. 2-5, the center Cp of the substantially spherically shaped seal unit 200 is defined as the point at which the longitudinal axis L of the assembly 100 and the center line C of the seal unit 200 intersect.

In general, the seal unit 200 can rotate freely within the housing. However, rotation of the seal unit 200 can be limited to prevent the seal unit 200 from rotating such that it obstructs the open proximal end 102a' of the housing 102. For example, in one exemplary embodiment, the seal unit 200 can be adapted to tip approximately 30 degrees in either direction (i.e., 30 degrees clockwise and 30 degrees counterclockwise) off of the longitudinal axis L. Such a configuration can ensure that an operator will be able to insert an instrument into the assembly 100 without being obstructed by the seal unit 200. Although the seal unit 200 can be adapted to rotate virtually any number of degrees about an axis of rotation, the exact degree of rotation will be determined by the size and shape of the instrument (i.e., an instrument with a larger diameter will have less degrees of rotation than an instrument with a relatively smaller diameter).

In use, an operator can insert an instrument into the open proximal end 102a' of the housing 102. The instrument can be received by the angular lead-in A formed in the seal unit 200 and guided through the seal element 220 into the working channel 106 of the assembly 100. The instrument need not be aligned with the longitudinal axis L of the assembly 100 upon insertion as the seal unit 200 can rotate to receive an instrument that is inserted off-axis or at an angle with respect to the longitudinal axis L. Once the instrument is advanced to a treatment site, the operator can further manipulate the instrument, and the seal unit 200 can continue to rotate in response to the movement of the instrument. Such a configuration can be effective to maintain the sealing engagement between the seal element 220 and the instrument as well as prevent non-uniform deformation of the seal element 220.

Although the seal unit is described herein primarily in the context of a spherically shaped element, one skilled in the art will appreciate that a variety of other designs can be utilized as long as they enable rotation of the seal unit as described above. By way of example, the seal unit need not form a complete sphere. It can be a hemisphere or a partial sphere that is truncated at one or both ends.

As indicated above, the seal unit 200 can include at least one seal element 220 that is adapted to selectively seal the working channel 106. Virtually any type of seal can be used to selectively seal the working channel 106. In one exemplary embodiment, the seal element 220 can take the form of a zero-closure seal, as such a seal can facilitate sealing both with and without an instrument present in the trocar assembly. FIGS. 2-5 illustrate one exemplary embodiment of a zero-closure seal. As shown, the seal element 220 takes the form of a multi-layer conical shaped, zero-closure seal. The conical shaped, zero-closure seal can include a series of overlapping seal segments that are assembled in a woven arrangement to provide a complete seal body. The seal segments can be stacked on top of one another or woven together in an overlapping fashion to form the multi-layer conical shaped seal shown in FIGS. 2-5. In use, an instrument can be inserted into the center of the seal assembly and the seal segments can engage an outer surface of the instrument to thereby prevent the passage of fluids through the housing.

The seal segments can be made from any number of materials known to those skilled in the art including, but not limited to, polyisoprene and silicone. The seal segments can also be molded such that they have a varying thickness across the profile of the seal. Varying the thickness across to the profile of the seal can be effective to minimize leakage and reduce drag forces on the instrument. Exemplary seal assembly embodiments are further described in U.S. Publication No. 2004/0230161, titled "Trocar Seal Assembly," filed on Mar. 31, 2004, and U.S. application Ser. No. 10/687,502, titled "Conical Trocar Seal," filed on Oct. 15, 2003, which are hereby incorporated by reference in their entirety.

Several techniques can be used to incorporate the seal element 220 into the spherically shaped member of the seal unit 200. For example, in one exemplary embodiment, the seal element 220 can be simply sandwiched between the upper and lower portions 202, 204 of the spherically shaped member and held in compression by the O- and U-ring 270, 280 components. In another embodiment, the seal element 220 can be trapped between the upper and lower portions 202, 204 utilizing techniques such as sonic welding and adhesives. In yet another embodiment, the seal element 220 and upper and lower portions 202, 204 of the spherically shaped member can be manufactured simultaneously to form one unitary structure.

The trocar assembly 100 can further include a second seal element 290. In general, the second seal element 290 can be disposed distal to the seal unit 200. Several types of seals can make up the second seal element 290. In one exemplary embodiment, shown in FIGS. 2-5, the second seal element 290 is a zero-closure duckbill seal that is positioned distal to the seal unit 200 in the housing 102. One skilled in the art will appreciate that virtually any type of seal can form the second seal element 290 including, but not limited to, duckbill seals, flapper valves, and flapper doors. Providing the trocar assembly 100 with first and second seal elements can eliminate the need for the proximally disposed seal element in the seal unit 200 to be a zero-closure seal. For example, the proximal seal element (i.e., the seal element 220 disposed in the seal unit 200) can be adapted to seal around an instrument that is present in the assembly 100 and the second seal element (i.e., the seal element 290 disposed distal to the seal unit 200) can be adapted to seal the trocar assembly 100 when no instrument is present. Thus, virtually any type of seal (including zero-closure seals as well as other types of seals) can be disposed in the seal unit 200.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A trocar assembly, comprising:
   a housing having a top portion, a bottom portion, and a cannula extending distally from the bottom portion, the housing and the cannula defining a working channel sized and configured to receive a surgical instrument; and
   a substantially spherically shaped seal unit disposed between the top and bottom portions of the housing and positioned distal to a proximal end of the top portion of the housing, the substantially spherically shaped seal unit being free to rotate within the housing when the top and bottom portions are locked together such that the top and bottom portions are fixed in relation to one another, the substantially spherically shaped seal unit having at least one seal element adapted to selectively seal the working channel, and the seal unit including a proximal portion with a proximal-facing convex outer surface, a distal portion with a distal-facing convex outer surface, and a bore extending through the proximal and distal portions and having the seal element extending thereacross;
   wherein the seal unit is adapted to rotate about at least one of a longitudinal axis of the assembly and an axis perpendicular thereto.

2. The trocar assembly of claim 1, wherein the at least one seal element is positioned between opposed poles of the substantially spherically shaped seal unit.

3. The trocar assembly of claim 1, wherein the at least one seal element is a zero-closure seal.

4. The trocar assembly of claim 1, wherein the substantially spherically shaped seal unit is rigid.

5. The trocar assembly of claim 1, wherein the substantially spherically shaped seal unit has angular lead-ins formed at proximal and distal ends of the bore.

6. The trocar assembly of claim 5, wherein a longitudinal axis of the bore aligns with the longitudinal axis of the working channel when the assembly is in a natural condition.

7. The trocar assembly of claim 1, wherein the spherically shaped seal unit is adapted to tip approximately 30 degrees clockwise and 30 degree counterclockwise about the longitudinal axis.

8. The trocar assembly of claim 1, wherein the spherically shaped seal unit is adapted to rotate freely with respect to an axis of rotation.

9. The trocar assembly of claim 1, further comprising a second seal element disposed distal to the seal unit.

10. The trocar assembly of claim 9, wherein the second seal element is a zero-closure seal.

11. The trocar assembly of claim 10, wherein the second seal element is a duckbill seal.

12. The trocar assembly of claim 1, wherein the top and bottom portions are configured to compress the seal unit therebetween.

13. The trocar assembly of claim 1, further comprising a proximal ring member and a distal ring member configured to capture the substantially spherically shaped seal unit therebetween, wherein the proximal and distal ring members are disposed between an outer surface of the substantially spherically shaped seal unit and an inner surface of the housing.

14. The trocar assembly of claim 13, wherein the proximal ring member is positioned proximal to the seal element and the distal ring member is positioned distal to the seal element.

15. The trocar assembly of claim 13, wherein the proximal and distal ring members are configured to seal around the perimeter of the substantially spherically shaped seal unit.

16. A trocar assembly, comprising:
    a housing having a top portion, a bottom portion, and a cannula extending distally from the bottom portion, the housing and the cannula defining a working channel sized and configured to receive a surgical instrument; and
    a seal unit disposed in the housing between the top and bottom portions, the seal unit being free to rotate within the housing when the top and bottom portions are locked together such that the top and bottom portions are fixed in relation to one another, the seal unit having a bore extending through a proximal pole and a distal pole of the seal unit and a seal element positioned between the proximal and distal poles substantially at a center line between the proximal and distal poles, wherein the proximal pole is positioned distal to a proximal end of the top portion of the housing, the seal unit being configured to allow off-axis insertion of an instrument through the working channel substantially without lateral movement of the seal unit.

17. The trocar assembly of claim 16, wherein the seal unit is adapted to rotate about at least one of a longitudinal axis of the assembly and an axis perpendicular thereto.

18. The trocar assembly of claim 16, wherein the at least one seal element is a zero-closure seal.

19. The trocar assembly of claim 16, wherein the at least one seal element is disposed in an approximately spherically shaped member.

20. The trocar assembly of claim 16, further comprising a second seal element disposed distal to the seal unit.

21. The trocar assembly of claim 20, wherein the second seal element is a zero-closure seal.

22. The trocar assembly of claim 21, wherein the second seal element is a duckbill seal.

23. The trocar assembly of claim 16, wherein the top and bottom portions are configured to compress the seal unit therebetween.

24. The trocar assembly of claim 16, further comprising a proximal ring member and a distal ring member configured to capture the seal unit therebetween, wherein the proximal and distal ring members are disposed between an outer surface of the seal unit and an inner surface of the housing.

25. A trocar assembly, comprising:
- a housing having a top portion, a bottom portion, and a cannula extending distally from the bottom portion, the housing and the cannula defining a working channel sized and configured to receive a surgical instrument; and
- a seal unit disposed within the housing and between the top and bottom portions, the seal unit having proximal and distal hemispheres and at least one seal element adapted to selectively seal the working channel, the seal unit including a bore extending therethrough with proximal and distal openings, and a seal element extending across the bore and defining an opening positioned distal to the proximal opening and proximal to the distal opening, wherein the proximal opening is distal to a proximal end of the top portion of the housing;
- wherein the seal unit is configured to rotate about its center when the top and bottom portions of the housing are locked together such that the top and bottom portions are fixed in relation to one another.

26. The trocar assembly of claim 25, wherein the top and bottom portions are configured to compress the seal unit therebetween.

27. The trocar assembly of claim 25, further comprising a proximal ring member and a distal ring member configured to capture the seal unit therebetween, wherein the proximal and distal ring members are disposed between an outer surface of the seal unit and an inner surface of the housing.

* * * * *